(12) United States Patent
Jeon et al.

(10) Patent No.: US 10,952,055 B2
(45) Date of Patent: Mar. 16, 2021

(54) WIRELESS COMMUNICATION SYSTEM, VEHICLE, SMART APPARATUS, AND CONTROLLING METHOD THEREOF

(71) Applicants: HYUNDAI MOTOR COMPANY, Seoul (KR); KIA MOTORS CORPORATION, Seoul (KR); LG ELECTRONICS INC., Seoul (KR)

(72) Inventors: Seul Ki Jeon, Suwon-si (KR); Nam Woong Hur, Hwaseong-si (KR); Eung Hwan Kim, Seoul (KR); Dong Woo Han, Seongnam-si (KR); Ge Nie Jang, Seoul (KR); Jeong Eun Shin, Seongnam-si (KR)

(73) Assignees: HYUNDAI MOTOR COMPANY, Seoul (KR); KIA MOTORS CORPORATION, Seoul (KR); LG ELECTRONICS INC., Seoul (KR)

( * ) Notice: Subject to any disclaimer, the term of this patent is extended or adjusted under 35 U.S.C. 154(b) by 678 days.

(21) Appl. No.: 15/823,158

(22) Filed: Nov. 27, 2017

(65) Prior Publication Data
US 2019/0014437 A1   Jan. 10, 2019

(30) Foreign Application Priority Data
Jul. 4, 2017   (KR) .................. 10-2017-0084915

(51) Int. Cl.
*H04W 4/80* (2018.01)
*B60W 40/08* (2012.01)
(Continued)

(52) U.S. Cl.
CPC ............. *H04W 4/80* (2018.02); *A61B 5/18* (2013.01); *B60K 28/04* (2013.01); *B60K 28/06* (2013.01);
(Continued)

(58) Field of Classification Search
CPC ......... H04W 4/80; H04W 4/48; H04W 76/10; A61B 5/18; A61B 5/02438; A61B 5/11;
(Continued)

(56) References Cited

U.S. PATENT DOCUMENTS

| 2008/0174451 A1 | 7/2008 | Harrington et al. |
| 2010/0137748 A1 | 6/2010 | Sone et al. |

(Continued)

FOREIGN PATENT DOCUMENTS

| KR | 10-2016-0016560 A | 2/2016 |
| KR | 10-2016-0094096 A | 8/2016 |

(Continued)

OTHER PUBLICATIONS

BT SPEC V4.2.*

*Primary Examiner* — Zhitong Chen
(74) *Attorney, Agent, or Firm* — Morgan, Lewis & Bockius LLP

(57) ABSTRACT

A wireless communication system includes a wearable device transmitting advertising packet data, a vehicle, and a smart apparatus. The vehicle receives the advertising packet data, connects with the wearable device if a user is present in the vehicle, and transmits set packet data to the smart apparatus. The smart apparatus receives the advertising packet data, connects with the wearable device if the user is not present in the vehicle, and receives the set packet data to disconnect the wearable device.

18 Claims, 6 Drawing Sheets

(51) Int. Cl.

| | | |
|---|---|---|
| *A61B 5/18* | (2006.01) | |
| *H04W 4/70* | (2018.01) | |
| *B60K 28/04* | (2006.01) | |
| *H04W 76/10* | (2018.01) | |
| *H04W 4/48* | (2018.01) | |
| *A61B 5/024* | (2006.01) | |
| *A61B 5/11* | (2006.01) | |
| *A61B 5/117* | (2016.01) | |
| *B60K 28/06* | (2006.01) | |

(52) U.S. Cl.
CPC ............. *B60W 40/08* (2013.01); *H04W 4/48* (2018.02); *H04W 4/70* (2018.02); *H04W 76/10* (2018.02); *A61B 5/02438* (2013.01); *A61B 5/11* (2013.01); *A61B 5/117* (2013.01); *B60W 2040/0818* (2013.01); *B60W 2040/0827* (2013.01); *B60W 2040/0872* (2013.01)

(58) Field of Classification Search
CPC ........ A61B 5/117; B60K 28/04; B60K 28/06; B60W 40/08; B60W 2040/0818; B60W 2040/0827; B60W 2040/0872
See application file for complete search history.

(56) References Cited

U.S. PATENT DOCUMENTS

| | | | |
|---|---|---|---|
| 2015/0338926 A1* | 11/2015 | Park | G06F 3/014 345/156 |
| 2016/0046294 A1* | 2/2016 | Lee | G06F 3/016 340/576 |
| 2016/0227009 A1* | 8/2016 | Kim | B60K 35/00 |
| 2017/0039845 A1 | 2/2017 | Lim et al. | |

FOREIGN PATENT DOCUMENTS

| | | |
|---|---|---|
| KR | 10-2016-0120101 A | 10/2016 |
| KR | 10-2017-0017590 A | 2/2017 |

\* cited by examiner

WIRELESS COMMUNICATION SYSTEM, VEHICLE, SMART APPARATUS, AND CONTROLLING METHOD THEREOF

CROSS-REFERENCE TO RELATED APPLICATION

This application is based on and claims the benefit of priority to Korean Patent Application No. 10-2017-0084915, filed on Jul. 4, 2017, in the Korean Intellectual Property Office, the disclosure of which is incorporated herein in its entirety by reference.

TECHNICAL FIELD

The present disclosure relates to a wireless communication system, a vehicle, a smart apparatus, and a controlling method of the wireless communication system, and more particularly, to a technology that controls a low-power wireless communication system.

BACKGROUND

With development of technologies of a smartphone and Internet of Things (IoT), various wearable devices have been recently released. The wearable devices are connected with other wireless communication devices or Internet by using low-power wireless communication schemes.

The wearable devices using the low-power wireless communication schemes may be connected with other wireless communication devices by a user setting or a driver's setting (configuration) or may be synchronized with communication devices.

SUMMARY

The present disclosure has been made to solve the above-mentioned problems occurring in the prior art while advantages achieved by the prior art are maintained intact.

An aspect of the present disclosure provides a wireless communication system, including a vehicle, a smart apparatus, etc., and a controlling method of the wireless communication system that automatically connects and disconnects a wireless communication device with and from another wireless communication device depending on whether a user is present in a vehicle, thereby skipping an additional setting operation of the user.

The technical problems to be solved by the present inventive concept are not limited to the aforementioned problems, and any other technical problems not mentioned herein will be clearly understood from the following description by those skilled in the art to which the present disclosure pertains.

According to an embodiment of the present disclosure, a wireless communication system includes a wearable device transmitting advertising packet data, a vehicle, and a smart apparatus. The vehicle receives the advertising packet data, connects with the wearable device if a user is present in the vehicle, and transmits set packet data to the smart apparatus. The smart apparatus receives the advertising packet data, connects with the wearable device if the user is not present in the vehicle, and receives the set packet data to disconnect the wearable device.

According to an embodiment, the advertising packet data may include data for setting BLE connection between the wearable device and the vehicle or the smart apparatus.

According to an embodiment, the wearable device periodically may transmit biometric information data to the vehicle or the smart apparatus.

According to an embodiment, the biometric information data may include data including at least one of heart rate information and motion information of the user.

According to an embodiment, the set packet data may include data indicating that the user is present in the vehicle.

According to an embodiment of the present disclosure, a vehicle includes a communication device receiving advertising packet data from a wearable device and to transmit set packet data to a smart apparatus and a controller controlling connection with the wearable device depending on whether a user is present in the vehicle and controlling the communication device such that the communication device transmits the set packet data to the smart apparatus if the user is present in the vehicle.

According to an embodiment, the set packet data may include data indicating whether the user is present in the vehicle.

According to an embodiment, the vehicle may further include a processor communicatively connected to the controller and configured to periodically receiving biometric information data of the user from the wearable device and determining a state of the user by using the received biometric information data.

According to an embodiment, the biometric information data may include data including at least one of heart rate information and motion information of the user.

According to an embodiment, the processor may provide a safe driving message corresponding to a current state of the user by using the biometric information data of the user.

According to an embodiment, the vehicle may further include a processor communicatively connected to the controller and configured to transmitting driving information of the vehicle to the wearable device.

According to an embodiment, the communication device may transmit the set packet data to a wireless communication device connected with the wearable device.

According to an embodiment of the present disclosure, a smart apparatus includes a communication device receiving advertising packet data from a wearable device and receiving set packet data from a vehicle and a controller connecting with the wearable device if a user is not present in the vehicle and to disconnect the wearable device if receiving the set packet data from the vehicle.

According to an embodiment, the set packet data may include data indicating whether the user is present in the vehicle.

According to an embodiment, the controller may restrict an operation of an installed application together with the wearable device.

According to an embodiment of the present disclosure, a controlling method of a wireless communication system includes steps of transmitting, by a wearable device, advertising packet data to a vehicle and a smart apparatus, receiving the advertising packet data and connecting with the wearable device by the vehicle if a user is present in the vehicle, transmitting, by the vehicle, set packet data to the smart apparatus, and receiving, by the smart apparatus, the set packet data to disconnect the wearable device.

According to an embodiment, the step of transmitting advertising packet data may include transmitting, by the wearable device, biometric information data.

According to an embodiment, the method may further include a step of providing, by the vehicle, a safe driving message corresponding to a current state of the user by using the biometric information data after the transmitting, by the wearable device, of the biometric information data.

According to an embodiment, the step of transmitting set packet data to the smart apparatus may include transmitting, by the vehicle, the set packet data to another wireless communication device connected with the wearable device.

According to an embodiment, the method may further include a step of restricting an operation of an application installed in the smart apparatus after disconnecting the wearable device.

BRIEF DESCRIPTION OF THE DRAWINGS

The above and other objects, features and advantages of the present disclosure will be more apparent from the following detailed description taken in conjunction with the accompanying drawings.

DETAILED DESCRIPTION

Figure 1:
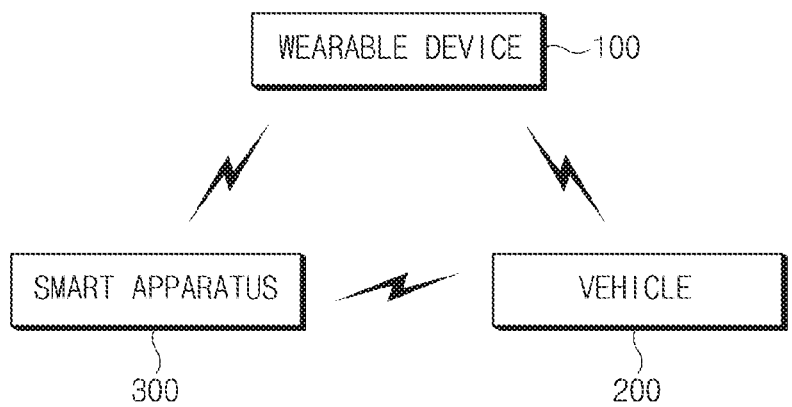
FIG. 1 is a block diagram for describing a wireless communication system, according to an embodiment of the present disclosure.

Hereinafter, exemplary embodiments of the present disclosure will be described in detail with reference to the accompanying drawings. In the drawings, the same reference numerals will be used throughout to designate the same or equivalent elements. In addition, a detailed description of well-known features or functions will be ruled out in order not to unnecessarily obscure the gist of the present disclosure.

In describing elements of exemplary embodiments of the present disclosure, the terms 1st, 2nd, first, second, A, B, (a), (b), and the like may be used herein. These terms are only used to distinguish one element from another element, but do not limit the corresponding elements irrespective of the order or priority of the corresponding elements. Unless otherwise defined, all terms used herein, including technical or scientific terms, have the same meanings as those generally understood by those skilled in the art to which the present disclosure pertains. It will be understood that terms used herein should be interpreted as having a meaning that is consistent with their meaning in the context of this disclosure and the relevant art and will not be interpreted in an idealized or overly formal sense unless expressly so defined herein.

A wireless communication system 10 according to an embodiment of the present disclosure may use a low-power wireless communication scheme such as Zigbee, Z-Wave, or Bluetooth Low Energy (BLE).

FIG. 1 is a block diagram for describing a wireless communication system, according to an embodiment of the present disclosure.

Referring to FIG. 1, the wireless communication system 10 according to an embodiment of the present disclosure may include a wearable device 100, a vehicle 200, and a smart apparatus 300.

The wearable device 100 that is an electronic device may be implemented with a smart watch, a smart band, a smart ring, or a smart glove that is wearable on a wrist, a finger, or an arm of a user.

The wearable device 100 may transmit advertising packet data (or ADV PACKET DATA). Herein, the advertising packet data may be data for setting BLE connection between the wearable device 100 and the vehicle 200 or the smart apparatus 300.

The wearable device 100 may periodically transmit biometric information data to the vehicle 200 or the smart apparatus 300. For example, the biometric information data may be data including at least one of heart rate information of a user received from a heart rate measuring device included in the wearable device 100 and motion information received from a sensor device included in the wearable device 100.

The vehicle 200 may receive the advertising packet data, may connect with the wearable device 100 in the case where the user is present in the vehicle 200, and may transmit set packet data to the smart apparatus 300. Herein, the set packet data may be data indicating that the user is present in a vehicle.

For example, the vehicle 200 may be an electronic device mounted in the vehicle 200. Alternatively, the vehicle 200 may be a vehicle control device that senses a state of the vehicle 200 and controls the vehicle 200 or an Audio, Video, Navigation (AVN) device mounted in the vehicle 200.

The vehicle 200 may include a user state determining device 210, a vehicle information providing device 220, a communication device 230, and a controller 240. The user state determining device 210 and the vehicle information providing device 220 are implemented with a hardware processor which executes software instructions stored in an associated non-transitory memory to thereby provide the functionalities of the user state determining device 210 and the vehicle information providing device 220. Details of the vehicle 200 will be described with reference to FIG. 3.

The controller 240 is an electric circuitry that executes instructions of software which thereby performs various functions described hereinafter.

The vehicle 200 may transmit the set packet data to another wireless communication device (or another wireless communication device connected with the wearable device 100) in addition to the smart apparatus 300. Herein, another wireless communication device may include various devices, which are capable of wirelessly communication, such as Bluetooth devices. This exemplification is to help understand the present disclosure, and an embodiment of the present disclosure may not be limited thereto.

The vehicle 200 may provide a safe driving message corresponding to a current state of the user by using the biometric information data received from the wearable device 100. For example, the user state determining device 210 included in the vehicle 200 may determine the current state of the user including driving inattention such as drowsiness and fatigue by using the biometric information data received from the wearable device 100 and may provide the safe driving message corresponding to the determined current state of the user.

The vehicle 200 may output the safe driving message to the user by using a cluster 201 or an information providing device 202 such as a display that is included in the vehicle 200. This exemplification is to help understand the present disclosure, and an embodiment of the present disclosure may not be limited thereto.

The vehicle 200 may transmit driving information of the vehicle 200 and state information of the vehicle 200, which are generated, to the wearable device 100 by using a network in the vehicle 200. The user may verify the driving information of the vehicle 200 by using the wearable device 100 or the smart apparatus 300.

The smart apparatus 300 may be a portable electronic device such as a smartphone or a tablet PC. The smart apparatus 300 may include a communication device 310 and a controller 320. Hereinafter, details about the smart apparatus 300 will be described with reference to FIG. 4.

The smart apparatus 300 may receive the advertising packet data from the wearable device 100 and may receive the set packet data from the vehicle 200. Herein, the advertising packet data may be data for setting BLE connection between the wearable device 100 and the smart apparatus 300. The set packet data may be data indicating that the user is present in a vehicle.

In a state where the smart apparatus 300 is connected with the wearable device 100 in the case where the user is not present in the vehicle 200, if the user is present in the vehicle 200, the smart apparatus 300 may receive of the set packet data from the vehicle 200 to disconnect the wearable device 100.

The smart apparatus 300 may restrict an operation of an application installed in the smart apparatus 300 after the receiving of the set packet data from the vehicle 200 to disconnect the wearable device 100, thereby preventing the distraction of the user occurring because the user utilizes the smart apparatus 300 during the driving of the vehicle 200.

Figure 2:
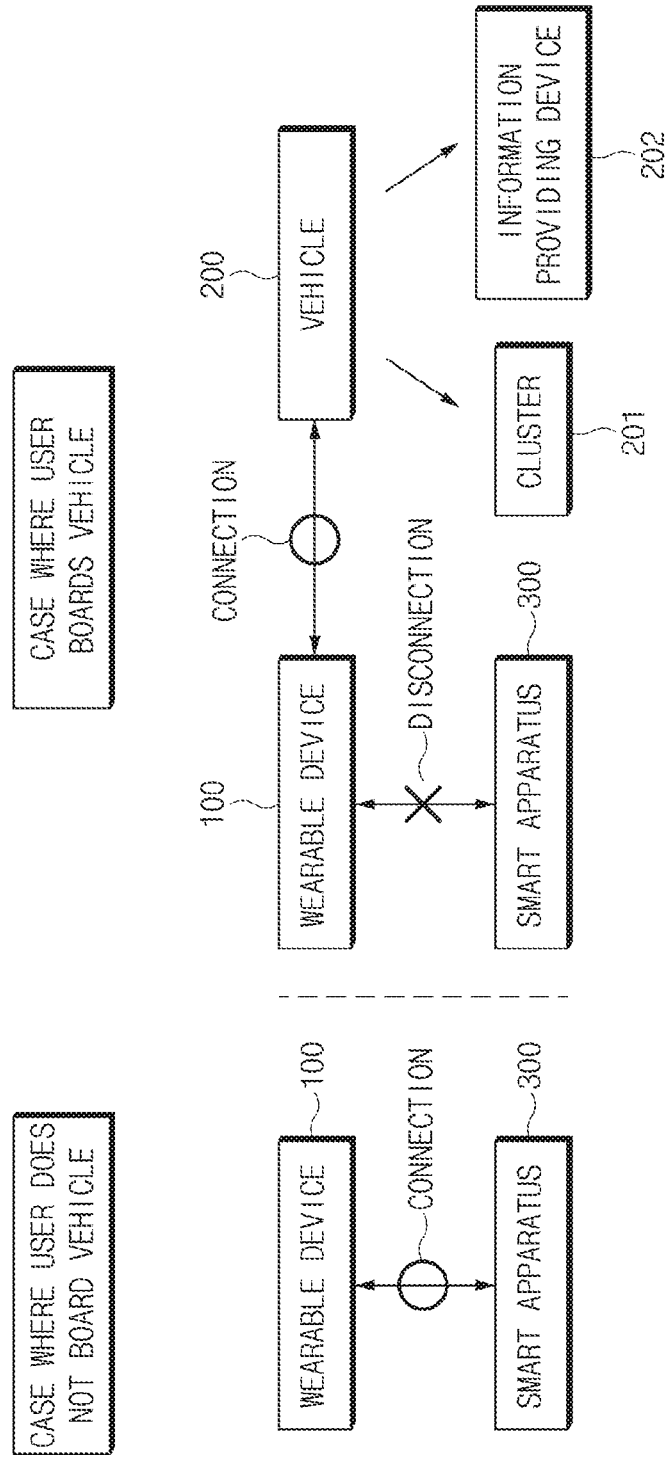
FIG. 2 is a diagram for describing an operating process of a wireless communication system, according to an embodiment of the present disclosure.

FIG. 2 is a diagram for describing an operating process of a wireless communication system, according to an embodiment of the present disclosure.

Referring to FIG. 2, after the wearable device 100 of the wireless communication system 10 is connected with the smart apparatus 300 while being worn on a body of the user, the wearable device 100 may synchronize data.

In the case where the user is not present in the vehicle 200, the wearable device 100 may be connected with the smart apparatus 300 by using BLE. For example, the wearable device 100 may continuously transmit advertising packet data, and the smart apparatus 300 may receive the advertising packet data from the wearable device 100. In the case where the smart apparatus 300 does not receive set packet data from the vehicle 200 (in the case where the user is not present in the vehicle 200), the smart apparatus 300 may be connected with the wearable device 100. Herein, the advertising packet data may be data for setting BLE connection between the wearable device 100 and the vehicle 200 or the smart apparatus 300.

Referring to FIG. 2, if the user is present in the vehicle 200 in a state where the wearable device 100 and the smart apparatus 300 of the wireless communication system 10 are connected, the vehicle 200 may connect with the wearable device 100 in a state where the vehicle 200 receives the advertising packet data from the wearable device 100 and may transmit set packet data to the smart apparatus 300.

The smart apparatus 300 receiving the set packet data may restrict the use of the smart apparatus 300 of the user during the driving of the vehicle 200 by disconnecting the wearable device 100 and restricting an operation of an application installed in the smart apparatus 300.

Figure 3:
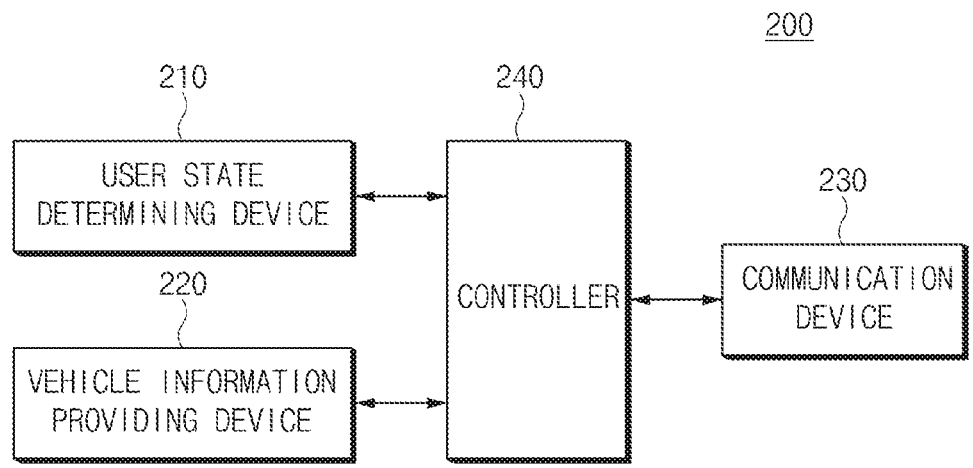
FIG. 3 is a block diagram for describing a vehicle, according to an embodiment of the present disclosure.

FIG. 3 is a block diagram for describing a vehicle, according to an embodiment of the present disclosure.

Referring to FIG. 3, the vehicle 200 may include the user state determining device 210, the vehicle information providing device 220, the communication device 230, and the controller 240.

The user state determining device 210 may periodically receive biometric information data of a user from the wearable device 100 and may determine a state of the user by using the received biometric information data. Herein, the biometric information data may be data including at least one of heart rate information and motion information of the user.

For example, the user state determining device 210 may provide a safe driving message corresponding to a current state of the user by using the biometric information data of the user.

For example, the user state determining device 210 may determine the current state of the user including driving inattention such as drowsiness and fatigue by using biometric information data received from the wearable device 100 and may provide the safe driving message corresponding to the determined current state of the user.

For example, the user state determining device 210 may output the safe driving message to the user by using the cluster 201 or the information providing device 202 such as a display that is included in the vehicle 200. This exemplification is to help understand the present disclosure, and an embodiment of the present disclosure may not be limited thereto.

The vehicle information providing device 220 may transmit driving information and state information of the vehicle 200 to the wearable device 100. For example, the user state determining device 210 may transmit the driving information of the vehicle 200 and the state information of the vehicle 200, which are generated, to the wearable device 100 or the smart apparatus 300 by using a network in the vehicle 200. The user may verify the driving information of the vehicle 200 by using the wearable device 100 or the smart apparatus 300.

The communication device 230 may receive advertising packet data from the wearable device 100 and may transmit set packet data to the smart apparatus 300. Herein, the set packet data may be data indicating that the user is present in a vehicle.

The communication device 230 may transmit the set packet data to another wireless communication device in addition to the smart apparatus 300. Herein, another wireless communication device may include various devices, which are capable of wirelessly communication, such as Bluetooth devices. A Bluetooth device is to help understand the present disclosure, and an embodiment of the present disclosure may not be limited thereto.

The controller 240 may control connection with the wearable device 100 depending on whether the user is present in the vehicle 200. For example, the controller 240 may control the connection between the vehicle 200 and the wearable device 100 or may control the communication device 230 such that the communication device 230 transmits the set packet data to the smart apparatus 300.

The controller 240 may determine whether the user is present in the vehicle 200, by using various methods.

For example, a method of determining whether the user is present in the vehicle 200 may include the various methods such as recognizing, by a sensor installed in the vehicle 200, the registered user, recognizing, by the sensor installed in the vehicle 200, the registered wearable device 100, starting by the vehicle 200, or whether a door of the vehicle 200 is opened or closed. This exemplification is to help understand the present disclosure, and an embodiment of the present disclosure may not be limited thereto.

That is, if it is determined that the user is present in the vehicle 200, the controller 240 may control the connection between the vehicle 200 and the wearable device 100 and may control the communication device 230 such that the communication device 230 transmits the set packet data to the smart apparatus 300.

Figure 4:
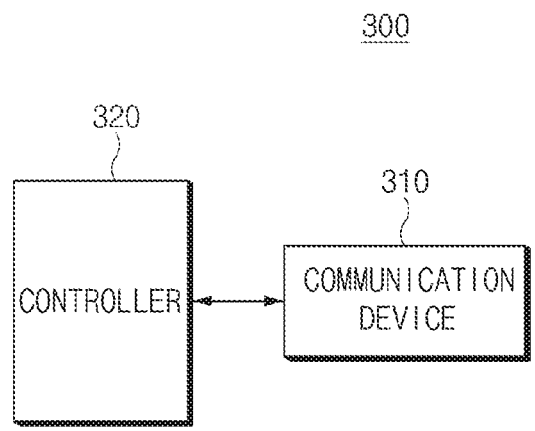
FIG. 4 is a block diagram for describing a smart apparatus, according to an embodiment of the present disclosure.

FIG. 4 is a block diagram for describing a smart apparatus, according to an embodiment of the present disclosure.

Referring to FIG. 4, the smart apparatus 300 may include the communication device 310 and the controller 320.

The communication device 310 may receive advertising packet data from the wearable device 100 and may receive set packet data from the vehicle 200. Herein, the set packet data may be data indicating that the user is present in a vehicle.

If the user is present in the vehicle 200 in a state where the smart apparatus 300 is connected with the wearable device 100, the controller 320 may receive the set packet data from the vehicle 200 to disconnect the wearable device 100.

If receiving the set packet data from the vehicle 200, after disconnecting the wearable device 100, the controller 320 may restrict an operation of an application installed in the smart apparatus 300. For example, the controller 320 may prevent the distraction of the user occurring because the user utilizes the smart apparatus 300 during the driving of the vehicle 200.

Figure 5:
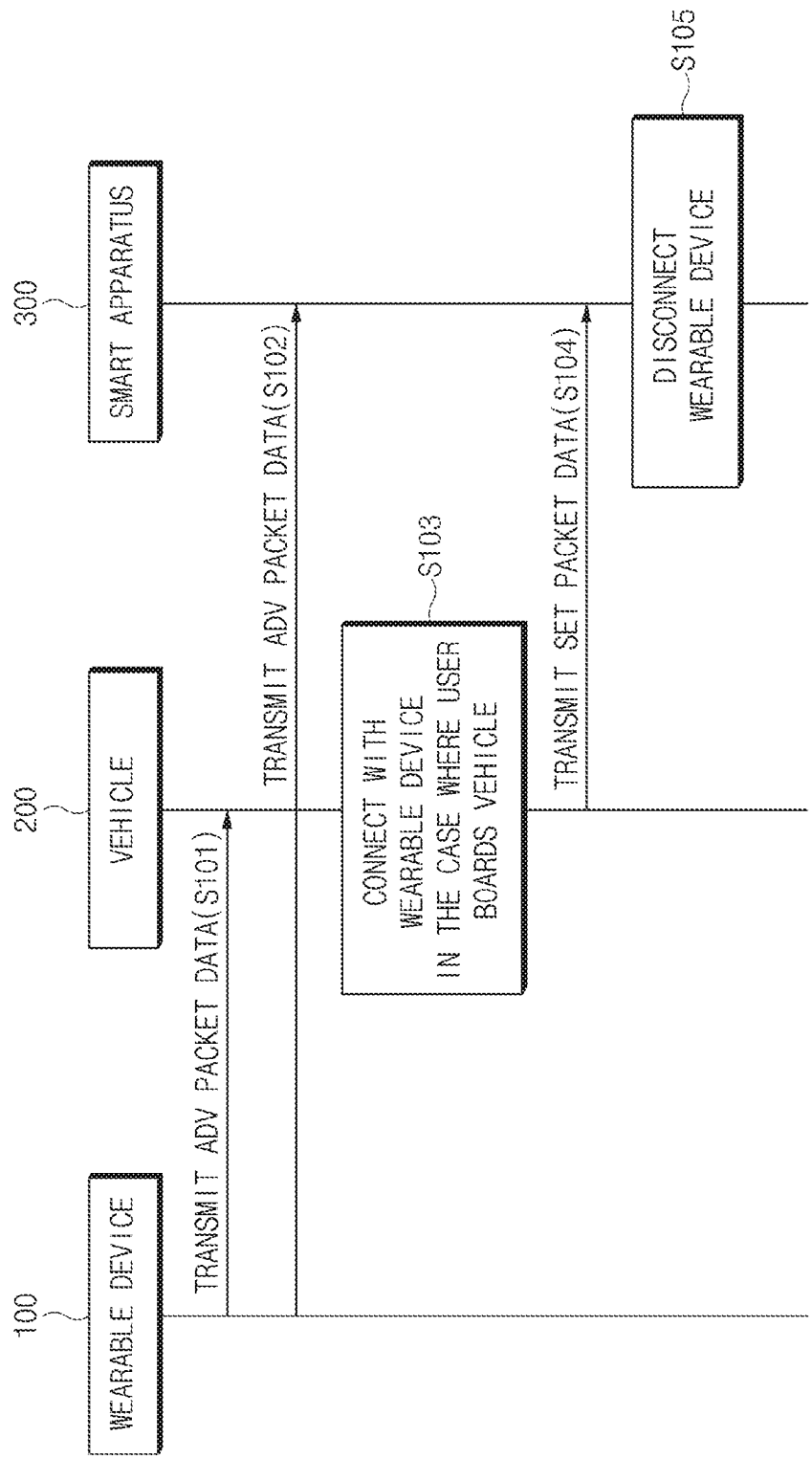
FIG. 5 is a diagram for describing a controlling method of a wireless communication system, according to an embodiment of the present disclosure.

FIG. 5 is a diagram for describing a controlling method of a wireless communication system, according to an embodiment of the present disclosure.

Referring to FIG. 5, a controlling method of the wireless communication system 10 according to an embodiment of the present disclosure may include transmitting (operation S101 and operation S102), by the wearable device 100, advertising packet data to the vehicle 200 and the smart apparatus 300, connecting the vehicle 200 with the wearable device 100 in the case where the vehicle 200 receives advertising packet data and the user is present in the vehicle 200 (operation S103), transmitting, by the vehicle 200, set packet data to the smart apparatus 300 (operation S104), and receiving, by the smart apparatus 300, the set packet data to disconnect the wearable device 100 (operation S105).

Hereinafter, operation S101 to operation S105 will be described with reference to FIGS. 1 and 2 in detail.

In operation S101 and operation S102, the wearable device 100 transmits the advertising packet data to the vehicle 200 and the smart apparatus 300. Herein, the advertising packet data may be data for setting BLE connection between the wearable device 100 and the vehicle 200 or the smart apparatus 300.

In the wireless communication system 10 according to an embodiment of the present disclosure, the wearable device 100 may transmit biometric information data as well as the advertising packet data to the vehicle 200 and the smart apparatus 300. Herein, the biometric information data may be data including at least one of heart rate information and motion information of the user.

In addition, after transmitting the advertising packet data to the vehicle 200 and the smart apparatus 300, the wearable device 100 may transmit the biometric information data. Alternatively, the wearable device 100 may transmit the biometric information data and the advertising packet data to the vehicle 200 and the smart apparatus 300 at the same time. This exemplification is to help understand the present disclosure, and an embodiment of the present disclosure may not be limited thereto.

In operation S103, the vehicle 200 receives the advertising packet data and may connect the vehicle 200 with the wearable device 100 in the case where the user is present in the vehicle 200.

Furthermore, the vehicle 200 may provide a safe driving message corresponding to a current state of the user by using the biometric information data.

For example, the vehicle 200 may output the safe driving message to the user by using the cluster 201 or the information providing device 202 that are included in the vehicle 200. This exemplification is to help understand the present disclosure, and an embodiment of the present disclosure may not be limited thereto.

In operation S104, the vehicle 200 transmits set packet data to the smart apparatus 300. Herein, the set packet data may be data indicating that the user is present in a vehicle.

Moreover, the vehicle 200 may transmit the set packet data to another wireless communication device in addition to the smart apparatus 300. Herein, another wireless communication device may include various devices, which are capable of wirelessly communication, such as Bluetooth devices. A Bluetooth device is to help understand the present disclosure, and an embodiment of the present disclosure may not be limited thereto.

In operation S105, the smart apparatus 300 may receive the set packet data from the vehicle 200 to release the connection between the smart apparatus 300 and the wearable device 100. The smart apparatus 300 may restrict an operation of an application installed in the smart apparatus 300, thereby preventing the distraction of the user occurring because the user utilizes the smart apparatus 300 during the driving of the vehicle 200.

Figure 6:
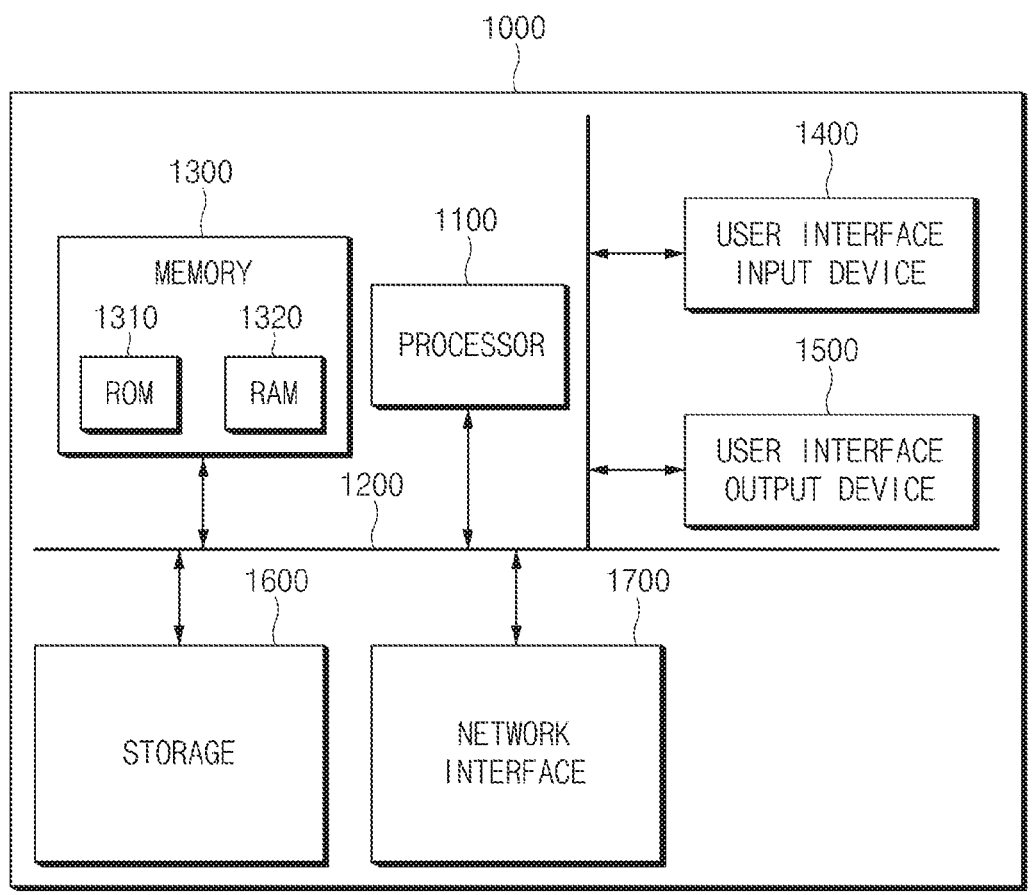
FIG. 6 is a block diagram illustrating a computing system performing a controlling method of a wireless communication system, according to an embodiment of the present disclosure.

FIG. 6 is a block diagram illustrating a computing system performing a controlling method of a wireless communication system, according to an embodiment of the present disclosure.

Referring to FIG. 6, a computing system 1000 may include at least one processor 1100, a memory 1300, a user interface input device 1400, a user interface output device 1500, a storage 1600, and a network interface 1700, which are connected with each other via a bus 1200.

The processor 1100 may be a central processing device (CPU) or a semiconductor device that processes instructions stored in the memory 1300 and/or the storage 1600. Each of the memory 1300 and the storage 1600 may include various types of volatile or non-volatile storage media. For example, the memory 1300 may include a read only memory (ROM) and a random access memory (RAM).

Thus, the operations of the methods or algorithms described in connection with the embodiments disclosed in the specification may be directly implemented with a hardware module, a software module, or combinations thereof, executed by the processor 1100. The software module may reside on a storage medium (e.g., the memory 1300 and/or the storage 1600) such as a RAM, a flash memory, a ROM, an erasable and programmable ROM (EPROM), an electrically EPROM (EEPROM), a register, a hard disc, a removable disc, or a compact disc-ROM (CD-ROM). The storage medium may be coupled to the processor 1100. The processor 1100 may read out information from the storage medium and may write information in the storage medium. Alternatively, the storage medium may be integrated with the processor 1100. The processor and storage medium may reside in an application specific integrated circuit (ASIC). The ASIC may reside in a user terminal. Alternatively, the processor and storage medium may reside as a separate component in the user terminal.

According to an embodiment of the present disclosure, a wireless communication system, a vehicle, a smart apparatus, and a controlling method of the wireless communication system that automatically connect and disconnect a wireless communication device with and from another wireless communication device, thereby skipping an additional setting operation of the user.

According to an embodiment of the present disclosure, a wireless communication system, a vehicle, a smart apparatus, and a controlling method of the wireless communication system that perform connection and disconnection between wireless communication devices depending on whether a user is present in a vehicle.

According to an embodiment of the present disclosure, a wireless communication system, a vehicle, a smart apparatus, and a controlling method of the wireless communication system that restrict a setting operation of a wireless communication device such as a smart apparatus of a user, thereby preventing the distraction of the user in advance during the driving of the vehicle 200.

Hereinabove, although the present disclosure has been described with reference to exemplary embodiments and the accompanying drawings, the present disclosure is not limited thereto, but may be variously modified and altered by those skilled in the art to which the present disclosure pertains without departing from the spirit and scope of the present disclosure claimed in the following claims.

Therefore, embodiments of the present disclosure are not intended to limit the technical spirit of the present disclosure, but provided only for the illustrative purpose. The scope of protection of the present disclosure should be construed by the attached claims, and all equivalents thereof should be construed as being included within the scope of the present disclosure.

What is claimed is:

1. A wireless communication system comprising:
   a wearable device configured to transmit advertising packet data;
   a vehicle; and
   a smart apparatus,
   wherein the vehicle receives the advertising packet data, connects with the wearable device if a user is present in the vehicle, and transmits set packet data to the smart apparatus;
   wherein the smart apparatus receives the advertising packet data, connects with the wearable device if the user is not present in the vehicle, and receives the set packet data to disconnect the wearable device; and
   wherein the smart apparatus restricts an operation of an installed application together with the wearable device after disconnecting the wearable device.

2. The wireless communication system of claim 1, wherein the advertising packet data includes data for setting Bluetooth Low Energy (BLE) connection between the wearable device and the vehicle or the smart apparatus.

3. The wireless communication system of claim 1, wherein the wearable device periodically transmits biometric information data to the vehicle or the smart apparatus.

4. The wireless communication system of claim 3, wherein the biometric information data includes data including at least one of heart rate information and motion information of the user.

5. The wireless communication system of claim 1, wherein the set packet data includes data indicating that the user is present in the vehicle.

6. A vehicle comprising:
   a communication device configured to receive advertising packet data from a wearable device and to transmit set packet data to a smart apparatus; and
   a controller configured to control connection with the wearable device depending on whether a user is present in the vehicle and to control the communication device such that the communication device transmits the set packet data to the smart apparatus if the user is present in the vehicle,
   wherein the control device restricts an operation of an installed application together with the wearable device after disconnecting the wearable device.

7. The vehicle of claim 6, wherein the set packet data includes data indicating whether the user is present in the vehicle.

8. The vehicle of claim 6, further comprising:
   a processor communicatively connected to the controller and configured to:
   periodically receive biometric information data of the user from the wearable device and to determine a state of the user by using the received biometric information data.

9. The vehicle of claim 8, wherein the biometric information data includes data including at least one of heart rate information and motion information of the user.

10. The vehicle of claim 8, wherein the processor provides a safe driving message corresponding to a current state of the user by using the biometric information data of the user.

11. The vehicle of claim 6, further comprising:
    a processor communicatively connected to the controller and configured to:
    transmit driving information of the vehicle to the wearable device.

12. The vehicle of claim 6, wherein the communication device transmits the set packet data to a wireless communication device connected with the wearable device.

13. A smart apparatus comprising:
    a communication device configured to receive advertising packet data from a wearable device and to receive set packet data from a vehicle; and
    a controller configured to connect with the wearable device if a user is not present in the vehicle and to disconnect the wearable device if receiving the set packet data from the vehicle,
    wherein the control device restricts an operation of an installed application together with the wearable device after disconnecting the wearable device.

14. The smart apparatus of claim 13, wherein the set packet data includes data indicating whether the user is present in the vehicle.

15. A controlling method of a wireless communication system, the method comprising steps of:
    transmitting, by a wearable device, advertising packet data to a vehicle and a smart apparatus;
    receiving the advertising packet data and connecting with the wearable device by the vehicle if a user is present in the vehicle;
    transmitting, by the vehicle, set packet data to the smart apparatus;
    receiving, by the smart apparatus, the set packet data to disconnect the wearable device; and
    restricting an operation of an application installed in the smart apparatus after disconnecting the wearable device.

16. The method of claim 15, wherein the step of transmitting advertising packet data includes transmitting, by the wearable device, biometric information data.

17. The method of claim 16, further comprising a step of:
  providing, by the vehicle, a safe driving message corresponding to a current state of the user by using the biometric information data after the transmitting, by the wearable device, of the biometric information data.

18. The method of claim 15, wherein the step of transmitting set packet data to the smart apparatus includes:
  transmitting, by the vehicle, the set packet data to another wireless communication device connected with the wearable device.

* * * * *